United States Patent [19]

Fodor et al.

[11] Patent Number: 5,214,045
[45] Date of Patent: May 25, 1993

[54] AMINO ACID CONTAINING ACRYLAMIDE DERIVATIVES FOR ULCER PREVENTION OR TREATMENT

[75] Inventors: Tamas Fodor; Janos Fischer; Laszlo Dobay; Elemer Ezer; Judit Matuz, Saghy; Katalin; Laszlo Szporny; György Hajos, all of Budapest, Hungary

[73] Assignee: Richter Gedeon Vegyeszeti Gyar RT, Budapest, Hungary

[21] Appl. No.: 551,518

[22] Filed: Jul. 11, 1990

[30] Foreign Application Priority Data

Jul. 14, 1989 [HU] Hungary ................ 3571/89

[51] Int. Cl.$^5$ .............. A61K 31/50; A61K 31/41; C07D 241/04; C07C 301/02
[52] U.S. Cl. ................ 514/255; 514/365; 514/423; 514/506; 544/391; 544/394; 544/395; 548/200; 548/530; 560/12; 562/443
[58] Field of Search ......... 544/391; 548/200, 530; 560/12; 562/443; 514/255, 365, 423, 506

[56] References Cited

U.S. PATENT DOCUMENTS 4,308,392 12/1981 Petrillo, Jr. et al. ............ 548/201
4,483,861 11/1984 Iwao et al. ............ 548/201

FOREIGN PATENT DOCUMENTS 0190685 8/1986 European Pat. Off. ........ 544/391
527919 7/1975 Japan .
527920 7/1975 Japan .
52-151121 12/1977 Japan .
52-151123 12/1977 Japan .

OTHER PUBLICATIONS

Miyamoto et al.; Chemical Abstract, vol. 87, 1977, #5393 m.
Solomons; Organic Chemistry IInd Ed., John Wiley and Sons, 1980 p. 653.

Primary Examiner—John M. Ford
Assistant Examiner—Y. N. Gupta
Attorney, Agent, or Firm—Herbert Dubno; Jonathan Myers

[57] ABSTRACT

Novel acrylic amide derivatives of the Formula (I)

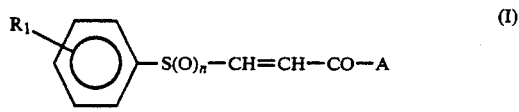

wherein
$R^1$ represents a hydrogen or a halogen atom or a $C_{1-4}$alkyl, a $C_{1-4}$alkoxy or a nitro group.
n is an integer of 0 to 2,
A represents an amino acid residue derived from a naturally occurring amino acid or an antipode thereof which is bonded to the acrylic acyl residue through its amino group; or a residue derived from thiazolidinecarboxylic acid, bonded to the acrylic acyl group through its nitrogen, or a derivative of the above residues wherein any free carboxy group is esterified with a $C_{1-4}$alkyl group or is amidated; or A represents a group of the formula

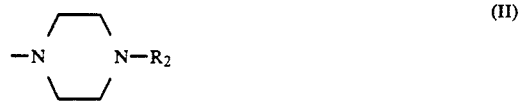

wherein $R_2$ is a hydrogen atom or a phenyl, $C_{1-4}$alkyl or $C_{1-4}$alkoxycarbonyl group,
and their salts which have cytoprotective and antiulcer to activities. A process is also described for the preparation of said compounds.

14 Claims, No Drawings

AMINO ACID CONTAINING ACRYLAMIDE DERIVATIVES FOR ULCER PREVENTION OR TREATMENT

The present invention is concerned with novel acrylic amide derivatives, their preparation, pharmaceutical formulations containing them and their use in medicine, particularly in the prophylaxis and treatment of ulcers.

According to a first aspect of the present invention, there is provided a novel compound of formula

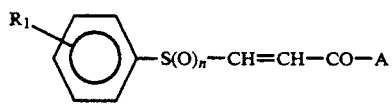

wherein
$R_1$ represents a hydrogen or a halogen atom or a $C_{1-4}$alkyl, a $C_{1-4}$alkoxy or a nitro group,
n is an integer of 0 to 2,
A represents an amino acid residue derived from a naturally occurring amino acid or an antipode thereof which is bonded to the acrylic acyl residue through its amino group; or a residue derived from thiazolidinecarboxylic acid bonded to the acrylic acyl group through its nitrogen; or a derivative of the above residues wherein any free carboxy group is esterified with a $C_{1-4}$alkyl group or is amidated; or A represents a group of formula

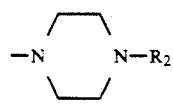

wherein $R_2$ is a hydrogen atom or a phenyl, a $C_{1-4}$alkyl or a $C_{1-4}$alkoxycarbonyl group,
and salts thereof.

As for the structurally closest compounds, reference is made to the compounds of the formula

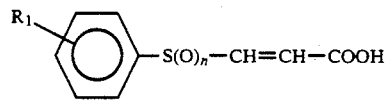

which can be used as starting material in the process of the invention.

The preparation of the compounds of formula (III) or sodium salts thereof as well as their non-pharmaceutical use have been described in a number of papers and patent specifications.

Those compounds of formula (III), wherein n is zero, and analogous compounds being different only in the meaning of $R_1$ are referred to hereinafter as phenylthiopropenoic acid derivatives.

Those compounds of formula (III) wherein n is 1, and analogous compounds being different only in the meaning of $R_1$ are referred to hereinafter as phenylsulfinylpropenoic acid derivatives.

Those compounds of formula (III), wherein n is 2, and analogous compounds being different only in the meaning of $R_1$, are referred to hereinafter as phenylsulfonylpropenoic acid derivatives.

U.S. Pat. No. 2,532,291 describes the preparation of phenylthiopropenoic acid derivatives. No teaching is disclosed, however, concerning their use.

Japanese laid-open patent specifications 52-7919 and 52-7920 disclose the preparation of phenylthio-, phenylsulfinyl- and phenylsulfonylpropenoic acid derivatives and their alkali metal salts. The compounds prepared in JP 52-7919 are declared as surface active agents.

Japanese laid-open patent specification 151,121 discloses the preparation of phenylthiopropenoic acid derivatives and their alkali metal salts. These compounds are stated to be surface active agents and antibacterial agents and are suggested to be used as detergents, bactericidal or disinfecting agents, furthermore as cream bases.

Japanese laid-open patent specification 151,123 describes the preparation of phenylsulfinyl- and phenylsulfonylpropenoic acid derivatives. Alkali metal and alkaline earth metal salts of these compounds are also claimed but are not prepared. The use of these compounds as antibacterial agents, disinfecting agents, antifungal agents against mould as well as antioxidants is suggested.

European patent specification 40359 describes certain phenylsulfinylpropenoic acid derivatives useful as intermediates in the preparation of dyestuffs.

Surprisingly we have found, that the compounds of formula (I) and their salts can also be used as human medicaments in particular for the pre- and after-treatment of patients having or prone to have ulceration.

A steadily increasing part of the population is involved in the ulceration of the digestive tract. Ulcers induce a very strong pain in its active stage and bleeding can also occur. According to traditional medication, the primary object is to reduce the pain, then to promote the healing of the injured tissues. Traditional medicaments (e.g. Pyrenzepine, Cimetidine, Omeprazole, etc.) have been intended to achieve the above effects by the reduction of the gastric acid level and inhibition of the secretion of gastric acid, respectively. In the case of proper medication and diet, an ulcer is generally healed after 4 to 6 weeks. However, it happens frequently that the ulcer relapses and the medication should be recommenced.

Recent investigations are focussed increasingly to the so-called cytoprotective compounds. These compounds increase the protective ability of the stomach thereby upon the administration of such compounds the probability of a relapse of an ulcer is significantly reduced or the emergence of an ulcer can be prevented in a subject susceptible to an ulcer.

Compounds exerting inhibitory activity on gastric acid secretion in addition to their cytoprotective activity are, of course, of particular interest.

Among the compounds of the present invention, there are several compounds having both cytoprotective and gastric acid secretion inhibitory activities. We have found, additionally, that the compounds of the invention exert prolonged action for both activities.

In the Tables below illustrating the results of biological investigations the following abbreviations are used:
A: diethyl N-[3-phenylsulfinyl-2(E)-propenoyl]-(R)-aspartate
B: diethyl N-[3-phenylsulfonyl-2(E)-propenoyl]-(R)-aspartate
C: 1-[3-phenylsulfonyl-2(E)-propenoyl]-4-phenylpiperazine D: methyl 2(S)-[3-phenylsulfonyl-2(E)-propenoylamino]-4-methylthiobutyrate E: diethyl N-[3-phenyltio-2(E)-propenoyl]-(R)-aspartate F: diethyl-N-[3-penylthio-2(E)-propenoyl]-(S)-aspartate G: 1-[3-phenylsulfonyl-2(E)-propenoyl]-2(S)-carbamoylpyrrolidine H: ethyl N-[3-phenylsulfonyl-2(E)-propenoyl]glycinate I: ethyl N-[3-phenylsulfonyl-1-2(E)-propenyl]-(S)-alanate J: methyl N-[3-phenylthio-2(Z)-propenoyl]-(R)-thiazolidine-4-carboxylate K: magnesium N-[3-phenylsulfonyl-2(E)-propenoyl]-(R)-aspartate.4H$_2$O.

The compounds of the invention were tested for their biological activity by the following methods.

1) Assay of gastric injuries induced by acidic alcohol [A. Robert, Gastroenterology, 77, 761–767 (1979)]

Female rats weighing about 120 to 150 g fasted for 24 hours were used in this test. Test compounds suspended with Tween 80 were given orally to the animals through an intragastric tube. After a certain period (pretreatment time) acidic alcohol was given through the intragastric tube at a dose or 0.5 ml per 100 g of body weight. The animals were sacrificed after 1 hour, their stomachs were removed and incised along the great curve. The length of the reddish-brown strips (haemorrhagic lesions) was measured and the mean total length per stomach was calculated. The biological activity of the test compounds was given and compared to that of the control group. the results are shown in Tables 1 and 2 below.

TABLE 1

| Compound | ED$_{50}$ p.o. (pretreatment: 30 min) |
| --- | --- |
| A | 2.1 mg/kg |
| B | 3.5 mg/kg |
| D | 3.5 mg/kg |
| G | 4.5 mg/kg |
| H | 1.6 mg/kg |
| I | 2.2 mg/kg |
| Reference compound: Sucralfat | 150 mg/kg |

TABLE 2

| Compound | % Inhibition at a dose of 10 mg/kg p.o. (pretreatment: 30 min) |
| --- | --- |
| E | 20 |
| F | 20 |
| J | 20 |

2) Assay of the inhibition of gastric acid secretion by using pylorus ligature
[Shay et al., Gastroenterology, 5, 43–61 (1945)]

Before ligating the pylorus, the test compounds suspended with Tween were given orally at a volume of 0.5 ml per 100 mg of body weight to female Wistar rats fasted previously for 20 hours. The animals were sacrificed 4 hours after the operation, and the amount of the acid in the stomach was measured by titration with 0.01N sodium hydroxide solution in the presence of phenolphthalein indicator. The pH value of the content of the stomach was measured by using a pH-meter (Radelkis, Type OP-211/1). The results are shown in Table 3.

TABLE 3

| Compound | % Inhibition in the amount of the acid at a dose of 25 mg/kg p.o. (pretreatment: 30 min) |
| --- | --- |
| A | 30 |
| C | 20 |
| E | 20 |
| F | 20 |
| G | 30 |
| H | 30 |
| I | 20 |
| K | 30 |

Therapeutic significance of the compounds according to the invention is further increased by the fact that they have bactericidal activity against Campylobacter pylori, the presence of which is a risk factor in the emergence of ulcers, or the healing of an ulcer of the digestive tract is influenced negatively by the presence of this bacterium [Internist, 29, 745–754, (1988)].

Toxicological data of the compounds of the invention are also beneficial. No death was observed when the compounds of the invention were given orally at a single dose of 1000 mg/kg of body weight.

According to a second aspect of the present invention, compounds of formula

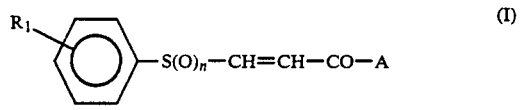

wherein
R$_1$ represents a hydrogen or a halogen atom or a C$_{1-4}$alkyl, a C$_{1-4}$alkoxy or a nitro group,
n is an integer of 0 to 2,
A represents an amino acid residue derived from a naturally occurring amino acid or an antipode thereof which is bonded to the acrylic acyl residue through its amino group; or a residue derived from thiazolidinecarboxylic acid bonded to the acrylic acyl group through its nitrogen; or a derivative of the above residues wherein any free carboxylic group is esterified with a C$_{1-4}$alkyl group or is amidated; or A represents a group of the formula

wherein R$_2$ is a hydrogen atom or a phenyl, a C$_{1-4}$alkyl or a C$_{1-4}$alkoxycarbonyl group,
and their salts may be prepared by any suitable process, for example
by reacting a compound of the formula

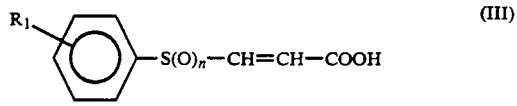

or a carboxyl-activated derivative thereof with a compound of formula

H-A (IV)

wherein $R_1$, n and A are as defined hereinbefore and, if desired, a) converting any ester group being present in a so-obtained compound to a free carboxy group by acidic hydrolysis and/or b) converting a so-obtained compound containing a free carboxy group to salt form, and/or c) oxidizing a so-obtained compound of formula (I) wherein n is zero or 1 and $R_1$ and A are as defined hereinbefore.

Compounds of formula (I) may be in (E) or (Z) configuration. Further, they may be isolated in anhydrous form or may be crystallised as mono- or oligohydrates.

Amidation reaction of the compounds of the formula (III) may be carried out preferably via their acyl chlorides which can be obtained preferably by treatment with thionyl chloride. The intermediate acyl chlorides generally are not isolated and purified but are used as crude products in the amidation reaction. Amidation reaction is carried out suitably in an inert organic solvent, preferably dioxane, at a temperature of between 0° C. and 40° C., preferably by starting with a lower temperature and then raising the reaction temperature gradually.

Alternatively, amidation reaction of a compound of formula (III) may be carried out by activation with dicyclohexylcarbodiimide. In this case the reaction is effectuated in an inert organic solvent, preferably dry dichloromethane and the temperature is kept in a range from 0° C. to 30° C., preferably by starting with a lower temperature and then heating the reaction mixture gradually.

Amidation can be effectuated by using other activated forms such as $C_{1-4}$alkyl esters or activation methods well known in peptide chemistry [see e.g. M. Bodánszk: Principles of Peptide Synthesis, p. 9 ff (1984) Springer Verlag]. Acidolysis of tert.butyl esters can be carried out by treatment with trifluoroacetic acid or with 6N hydrochloric acid in dioxane at room temperature.

Compounds of formula (I) containing free carboxy group(s) can be converted into salt form in a manner known in the art by treatment with pharmaceutically acceptable organic or inorganic bases.

Compounds of formula (I) wherein n is zero can be oxidized preferably in glacial acetic acid by treatment with a 30% solution of hydrogen peroxide to obtain a sulfoxide (n=1) when working at room temperature, while higher temperatures (e.g. about 80° C.) promote the formation of a sulfone (n=2).

Starting materials of formula (III) are well known and may be prepared by several methods described e.g. by H. Hogeveen [Recueil, 83, 813 (1964)].

Amine reactants of the amidation reaction e.g. naturally occurring amino acids and their antipodes or racemates, esters and amides are commercial products. Natural amino acids e.g. (S)-alanine, (S)-aspartic acid, (S)-methionine, (S)-proline, glycine, etc. may be used for this purpose.

Piperazine derivatives corresponding to the group of formula (II) are also commercially available.

According to a third aspect of the present invention, there are provided pharmaceutical compositions comprising, as active ingredient at least one compound of formula (I) and/or a pharmaceutically acceptable salt thereof with at least one pharmaceutical carrier or excipient, for parenteral or enteral administration. These pharmaceutical compositions may be used in the prophylaxis or treatment of ulcerations. The carrier or excipient must be nontoxic and pharmaceutically acceptable by the recipient, and may be a solid or liquid one. Suitable carriers are e.g. water, gelatin, lactose, starch, pectin, magnesium stearate, stearic acid, talc, vegetable oils such as peanut oil, olive oil, etc. The active ingredient may be formulated in a conventional manner e.g. to a solid composition such as a tablet, lozenge, dragee, capsule, e.g. gelatin capsule, pill, etc.

Pharmaceutical compositions of the invention optionally may contain one or more conventional excipients e.g. preservatives, stabilizing agents, wetting agents, emulgeators, etc. and further active ingredients exerting no synergistic activity in the given combination.

These formulations may be prepared by any suitable method, e.g. in case of solid formulations by sieving, admixing, granulating and compressing the ingredients. The so-obtained formulations may be subjected to conventional after-treatments well known in the pharmaceutical technology, e.g. sterilization. The amount of the active ingredient may be varied within a wide range, e.g. about from 0.01 to 95% by weight in these formulations.

A tablet formulation of the invention may contain in addition to the active ingredient a compression improving agent, such as microcrystalline cellulose, a disintegrator such as sodium starch glycollate, a polishing agent to ensure a shiny surface of the tablets such as calcium dihydrogen phosphate and a lubricant such as magnesium stearate.

A preferable capsule formulation of the invention may contain an inert diluent as mentioned above and a disintegrator as well as a lubricant.

Sterile aqueous solutions suitable for parenteral administration may contain in addition to the active ingredient(s) preferably 10 to 50% v/v of a glycol, such as propylene glycol and sodium chloride sufficient to prevent haemolysis.

According to a fourth aspect of the present invention, there is provided a method of treating or preventing ulceration in mammals inclusive of man by using a compound of formula (I) or a pharmaceutically acceptable salt thereof, or a pharmaceutical composition containing such a compound in an amount sufficient to ensure the desired healing or preventing effect.

According to a fifth aspect of the present invention, there is provided the use of a compound of formula (I) or a pharmaceutically acceptable salt thereof in the preparation of a pharmaceutical composition for the prophylaxis or treatment of ulceration in mammals, inclusive of man.

The dosage regimen of the active ingredient may be varied within a wide range depending on various factors such as the nature of the active ingredient in question, the species, age and body weight of the subject to be treated, the severity and symptoms of the disease, etc. therefore the exact dose must be prescribed by the physician individually in each case. In general, the dosage may vary about from 10 to 200 mg active ingredient per day per adult in case of enteral administration.

For a better understanding of the invention, the following non-limiting Examples are given by way of illustration.

EXAMPLE 1

Diethyl N-[3-phenylsulfinyl-2(E)-propenoyl]-(R)-aspartate

Diethyl N-[3-phenylthio-2(E)-propenoyl]-(R)-aspartate (3.51 g, 10 mmol) was dissolved in glacial acetic acid (30 ml) and a 30% solution of hydrogen peroxide (1.4 ml) was added and the mixture was stirred at room temperature for 36 hours, then diluted with water (100 ml) and extracted twice with dichloromethane (50 ml each). The organic phase was dried over anhydrous sodium sulfate, the solvents were evaporated and the residue was suspended in carbon tetrachloride and filtered to give a crude product which was recrystallised from toluene, yielding the desired product (2.3 g, 63%).

Melting point: 121° to 123° C.,
$[\alpha]_D^{25}$: +15.1° (c=1, ethanol).

EXAMPLE 2

Diethyl N-[3-phenylsulfonyl-2(E)-propenoyl]-(R)-aspartate

A mixture of 3-phenylsulfonyl-2(E)-propenoic acid (8.48 g, 40 mmol) and thionyl chloride (60 ml) was boiled for 1.5 hours, then the excess of thionyl chloride was removed by distillation. The residual solid acyl chloride was dissolved in dry dioxane (50 ml) and was added dropwise to a suspension of diethyl (R)-aspartate hydrochloride (9.02 g, 40 mmol) and triethylamine (11.08 g, 80 mmol) in dry dioxane (60 ml) at 5° C. The reaction mixture was stirred at room temperature for 20 hours, the triethylamine hydrochloride precipitated was filtered off and washed with dry dioxane. Dioxane was evaporated under reduced pressure, the residue was dissolved in dichloromethane (100 ml), and successively extracted with a 5% solution of sodium bicarbonate, water, 1N hydrochloric acid and water again. The organic layer was dried over anhydrous sodium sulfate. After evaporation of the solvent the solid residue was suspended in n-hexane and filtered to yield the desired product (12.86 g, 83%).

Melting point: 112° to 115° C,
$[\alpha]_D^{25}$: +17.3° (c=1, ethanol).

EXAMPLE 3

1-[3-Phenylsulfonyl-2(E)-propenoyl]-4-phenyl-piperazine

A mixture of 3-phenylsulfonyl-2(E)-propenoic acid (3.18 g, 15 mmol) and thionyl chloride (50 ml) was boiled for 1.5 hours, then the excess of thionyl chloride was removed by evaporation. The residual acyl chloride was dissolved in dry dioxane (50 ml) and added to a solution of N-phenylpiperazine (5.34 g, 33 mmol) in dioxane (25 ml) at +5° C. The reaction mixture was stirred for 15 hours, the precipitated salt was removed by filtration and dioxane was evaporated. The residue was dissolved in dichloromethane (60 ml) and successively extracted with a 5% solution of sodium bicarbonate, water, 1N hydrochloric acid and water. The organic layer was dried over anhydrous sodium sulfate. After the evaporation of dichloromethane, the solid residue was suspended in diethyl ether and filtered off to yield the desired product (2.69 g, 51%).

Melting point: 181° to 184° C.

EXAMPLE 4

Methyl 2(S)-[3-phenylsulfonyl-2(E)-propenoylamino]-4-methylthiobutyrate

A mixture of 3-phenylsulfonyl-2(E)-propenoic acid (6.36 g, 30 mmol) and thionyl chloride (50 ml) was boiled for 1.5 hours, then the excess of thionyl chloride was evaporated. The residue was dissolved in dry dioxane (50 ml) and added to a suspension of (S)-methionine methyl ester hydrochloride (5.98 g, 30 mmol) and triethylamine (8.31 g, 60 mmol) in dry dioxane (50 ml) at +5° C., then the reaction mixture was stirred at room temperature for 15 hours and the precipitate was filtered off. After evaporation of dioxane, the residue was dissolved in dichloromethane (60 ml) and successively extracted with a 5% solution of sodium bicarbonate, water, 1N hydrochloric acid and water. The organic layer was dried over anhydrous sodium sulfate. After evaporation of the solvent, the solid residue was recrystallised from benzene to yield the desired product (6.58 g, 62%).

Melting point: 131° to 132° C.,
$[\alpha]_D^{25}$: -33.4° (c=1, methanol).

EXAMPLE 5

Diethyl N-[3-phenylthio-2(E)-propenoyl]-(R)-aspartate

A mixture of 3-phenylthio-2(E)-propenoic acid (12.2 g, 67.7 mmol) and thionyl chloride (50 ml) was boiled for 2 hours; then the excess of thionyl chloride was evaporated. The residue was dissolved in dry dioxane (50 ml) and added to a suspension of diethyl (R)-aspartate hydrochloride (15.27 g, 67.7 mmol) and triethylamine (18.8 ml, 135.4 mmol) in dry dioxane (100 ml) at +5° C.; then the reaction mixture was stirred at room temperatue for 20 hours, the precipitated salt filtered off and dioxane evaporated. The residue was dissolved in dichloromethane (100 ml) and successively extracted with a 5% solution of sodium bicarbonate, water, 1N hydrochloric acid and water. The organic layer was dried over anhydrous sodium sulfate and the solvent was evaporated to give a solid residue which was recrystallised from cyclohexane yielding the desired product (18.84 g, 79%).

Melting point: 99° to 101° C.,
$[\alpha]_D^{25}$: +17.3° (c=1, ethanol).

EXAMPLE 6

Diethyl N-[3-phenylthio-2(E)-propenoyl]-(S)-aspartate

By the method of Example 5 but using diethyl (S)-aspartate hydrochloride, the desired product was obtained (71%).

Melting point: 100° to 102° C.,
$[\alpha]_D^{25}$: -17.1° (c=1, ethanol).

EXAMPLE 7

1-[3-Phenylthio-2(E)-propenoyl]-2(S)-carbamoylpyrolidine

3-Phenylthio-2(E)-propenoic acid (4.5 g, 25 mmol) was dissolved in dry dichloromethane (30 ml) and a solution of dicyclohexylcarbodiimide (5.15 g, 25 mmol) in dry dichloromethane (20 ml) was added at 0° C. The mixture was stirred at 0° C. for 1 hour than (S)-proline amide (2.85 g, 25 mmol) was added to the reaction mixture over 2 hours at 0° C., and the mixture was stirred for a further 10 hours at room temperature. The dicyclohexylurea precipitated was filtered off, the filtrate was successively extracted with a 5% solution of sodium bicarbonate, water, 1N hydrochloric acid and water again. The organic layer was dried over anhydrous magnesium sulfate then the solvent was evaporated and the residue was triturated with petroleum ether (b.p. 70° C.) to give the desired product (2.66 g, 39%).

Melting point: 50° to 54° C.,
$[\alpha]^{25}$: −31.9° (c=1, ethanol).

EXAMPLE 8

1-[3-Phenylsulfonyl-2(E)-propenoyl]-2(S)-carbamoyl-pyrrolidine

1-[3-Phenylthio-2(E)-propenoyl]-2(S)-carbamoylpyrrolidine prepared according to Example 7 (2.76 g, 10 mmol) was dissolved in glacial acetic acid (20 ml), a 30% solution of hydrogen peroxide (2.5 ml) was added; then the reaction mixture was stirred at 80° C. for 2 hours. After evaporation of the solvent, the residue was recrystallised from ethyl acetate to give the desired product (2.1 g, 68%).

Melting point: 157° to 158° C.,
$[\alpha]_D^{25}$: −49.6° (c=1, methanol).

EXAMPLE 9

Ethyl N-[3-phenylsulfonyl-2(E)-propenoyl]glycinate

A mixture of 3-phenylsulfonyl-2(E)-propenoic acid (6.36 g, 30 mmol) and thionyl chloride (50 ml) was boiled for 2 hours then the excess of thionyl chloride was evaporated. The residue was dissolved in dry dioxane (50 ml) and added to a suspension of ethyl glycinate hydrochloride (4.2 g, 30 mmol) and triethylamine (8.31 g, 60 mmol) in dry dioxane (50 ml). After stirring for 20 hours, the solid was filtered off and dioxane was evaporated. The residue was dissolved in dichloromethane (50 ml) and successively extracted with a 5% solution of sodium bicarbonate, water, 1N hydrochloric acid and water. The organic layer was dried over anhydrous sodium sulfate and the solvent was evaporated. The residue was recrystallised from benzene to give the desired product (4.1 g, 46%).

Melting point: 156° to 157° C.

EXAMPLE 10

Ethyl N-[3-phenylsulfonyl-2(E)-propenoyl]-(S)alanate

A mixture of 3-phenylsulfonyl-2(E)-propenoic acid (4.24 g, 20 mmol) and thionyl chloride (30 ml) was boiled for 2 hours, then the excess of thionyl chloride was evaporated. The residue was dissolved in dry dioxane (30 ml) and added to a suspension of ethyl (S)-alanate hydrochloride (3.1 g, 20 mmol) and triethylamine (5.6 g, 40 mmol) in dry dioxane (40 ml) at +5° C. After stirring for 20 hours, the precipitated solid was filtered off and dioxane evaporated. The residue was dissolved in dichloromethane (50 ml) and successively extracted with a 5% solution of sodium bicarbonate, water, 1N hydrochloric acid and water. The organic layer was dried over anhydrous sodium sulfate and the solvent evaporated. The residue was recrystallised from ethyl acetate to give the desired product (2.8 g, 45%).

Melting point: 174° to 177° C.,
$[\alpha]_D^{25}$: −9.2° (c=1, dichloromethane).

EXAMPLE 11

1-Ethoxycarbonyl-4-[3-phenylsulfonyl-2(E)-propenoyl]-piperazine

A solution of the acyl chloride prepared from 3-phenylsulfonyl-2(E)-propenoic acid (3.18 g, 15 mmol) and thionyl chloride in dry dioxane (50 ml) was added to a solution of 1-ethoxycarbonylpiperazine (5.2 g, 33 mmol) in dry dioxane (30 ml) at +5° C. After stirring for 20 hours, the precipitated salt was filtered off and dioxane was evaporated. The residue was dissolved in dichloromethane (50 ml) and successively extracted with a 5% solution of sodium bicarbonate, water, 1N hydrochloric acid and water. The organic layer was dried over anhydrous sodium sulfate and the solvent was evaporated to give a residue which was recrystallised from carbon tetrachloride to give the desired product (3.0 g, 57%).

Melting point: 116° to 117° C.

EXAMPLE 12

Methyl N-[3-phenylthio-2(Z)-propenoyl]-(R)-thiazolidine-4-carboxylate

3-Phenylthio-2(Z)-propenoic acid (5.4 g, 30 mmol) was dissolved in dry dichloromethane (20 ml) then dicyclohexylcarbodiimide (6.18 g, 30 mmol) was added to the solution at 0° C. After stirring for 1 hour, a solution of methyl (R)-thiazolidine-4-carboxylate hydrochloride (5.66 g, 30 mmol) in dry dichloromethane (20 ml), then a solution of N-methylmorpholine (3.03 g, 30 mmol) in dry dichloromethane (5 ml) were added to the reaction solution. After stirring for 20 hours, the solid was filtered off and the filtrate successively extracted with a 8% solution of sodium bicarbonate, water, 1N hydrochloric acid and water. The organic layer was dried over anhydrous magnesium sulfate. After evaporation of the solvent, the residue was recrystallised from acetonitrile to give the desired product (3.33 g, 36%).

Melting point: 126° to 128° C.,
$[\alpha]_D^{25}$: −191.4° (c=1, methanol).

EXAMPLE 13

Di-tert. Butyl N-[3-phenylsulfonyl-2(E)-propenoyl](R)-aspartate

A mixture of 3-phenylsulfonyl-2(E)-propenoic acid (6.36 g, 30 mmol) and thionyl chloride (50 ml) was boiled for 1 hours, then the excess of thionyl chloride was evaporated. The solid acyl chloride was dissolved in dry dioxane (50 ml) and added dropwise to a suspension of di-tert. butyl (R)-aspartate hydrochloride (8.45 g, 30 mmol) and triethylamine (8.3 ml) in dry dioxane (100 ml) at 0° C. The reaction mixture was stirred for 10 hours then the precipitated solid was filtered off and washed with dioxane. The dioxane was evaporated, the residue was dissolved in dichloromethane (100 ml) and successively extracted with a 5% solution of sodium bicarbonate, water, 1N hydrochloric acid and water. The organic layer was dried over anhydrous sodium sulfate. After evaporation of the solvent the solid residue was suspended in diethyl ether, filtered and washed with diethyl ether to give the desired product (10.1 g, 77%).

Melting point: 168° to 169° C.,
$[\alpha]_D^{25}$: +13.3° (c=1, methanol).

EXAMPLE 14

N-[3-Phenylsulfonyl-2(E)-propenoyl]-(R)-aspartic acid

A mixture of the di-tert.butyl ester prepared in Example 13 (4.4 g, 10 mmol) and 6N hydrochloric acid in dioxane (20 ml) was stirred for 4 hours then evaporated to dryness. After addition of benzene the residue was filtered off and dried to give the desired product (3.25 g, 99%).

Melting point: 183° to 184° C.,
$[\alpha]_D^{25}$: +7.3° (c=1, methanol).

EXAMPLE 15

Magnesium N-[3-phenylsulfonyl-2(E)-propenoyl]-(R)aspartate.4-$H_2O$

Triethylamine (2.22 ml, 16 mmol) was added dropwise to a suspension of the product of Example 14 (2.61 g, 8 mmol) in water (15 ml) and a solution of $MgCl_2.6H_2O$ (1.63 g) in water (5 ml) was added to the above solution then the whole mixture was stirred for 30 minutes. After evaporation of water, the residue was suspended in ethanol, filtered off and washed with ethanol to give the desired product (2.31 g, 83%).

$[\alpha]_D^{25}$: −3.9° (c=1, water).

Molecular formula: $C_{13}H_{11}MgNO_7S.4H_2O$ according to the elementary analysis data (Mw: 421.64).

We claim:

1. A compound of the Formula (I)

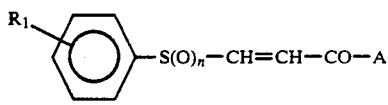

(I)

wherein
   $R_1$ represents a hydrogen or a halogen atom or a $C_{1-4}$alkyl, a $C_{1-4}$alkoxy or a nitro group;
   n is an integer of 0 to 2,
   A represents an amino acid radical derived from a naturally occurring amino acid selected from (s)-alanine, (s)-aspartic acid, (s)-methionine, (s)-proline or glycine which is bonded to the acrylic acyl radical through its amino group; or a radical derived from thiazolidinecarboxylic acid bonded to the acrylic acyl group through its nitrogen heteroatom; or a derivative of the above radical wherein any free carboxy group is esterified with a $C_{1-4}$alkyl group or is amidated; or A represents a group of the formula

(II)

wherein $R_2$ is a hydrogen atom or a phenyl, $C_{1-4}$alkyl or a $C_{1-4}$alkoxycarbonyl group, or a salt thereof.

2. Diethyl N-{3-phenylsulfinyl-2(E)-propenoyl}-(R)-aspartate or a pharmaceutically acceptable salt thereof as defined in claim 1.

3. Diethyl N-{3-phenylsulfonyl-2(E)-propenoyl}-(R)-aspartate or a pharmaceutically acceptable salt thereof as defined in claim 1.

4. 1-{3-phenylsulfonyl-2(E)-propenoyl}-4-phenyl piperazine or a pharmaceutically acceptable salt thereof as defined in claim 1.

5. Methyl 2(S)-{3-phenylsulfonyl-2(E)-propenoylamino}-4-methylthiobutyrate or a pharmaceutically acceptable salt thereof as defined in claim 1.

6. Diethyl N-{3-phenylthio-2(E)-propenoyl}-(R)-aspartate or a pharmaceutically acceptable salt thereof as defined in claim 1.

7. Diethyl N-{3-phenylthio-2(E)-propenoyl)-(S)-aspartate or a pharmaceutically acceptable salt thereof as defined in claim 1.

8. 1-{3-phenylsulfonyl-2(E)-propenoyl}-2(S)-carbamoyl-pyrrolidine or a pharmaceutically acceptable salt thereof as defined in claim 1.

9. Ethyl N-{3-phenylsulfonyl-2(E)-propenoyl}glycinate or a pharmaceutically acceptable salt thereof as defined in claim 1.

10. Ethyl N-{3-phenylsulfonyl-2(E)-propenoyl}-(S)-alanate or a pharmaceutically acceptable salt thereof as defined in claim 1.

11. Methyl N-{3-phenylthio-2(Z)-propenoyl}-(R)-thiazolidine-4-carboxylate or a pharmaceutically acceptable salt thereof as defined in claim 1.

12. Magnesium N-{3-phenylsulfonyl-2(E)-propenoyl}-(R)-aspartate.$4H_2O$ as defined in claim 1.

13. A pharmaceutical composition for the treatment or prevention of an ulcer which comprises a therapeutically effective amount of a compound of the Formula (I) as defined in claim 1 or a pharmaceutically acceptable salt thereof in combination with a pharmaceutically acceptable inert carrier.

14. A method of treating or preventing an ulcer in the digestive tract of a mammalian subject, which comprises the step of administering to said mammalian subject, a therapeutically effective amount of a compound of the Formula (I) as defined in claim 1 or a pharmaceutically acceptable salt thereof.

* * * * *